US007876877B2

(12) United States Patent
Stockl (10) Patent No.: US 7,876,877 B2
(45) Date of Patent: Jan. 25, 2011

(54) DENTAL X-RAY APPARATUS COMPRISING A PATIENT-POSITIONING SYSTEM ARRANGED ON A SUPPORT AND PROVIDED WITH A FOREHEAD REST

(75) Inventor: Klaus Stockl, Bensheim (DE)

(73) Assignee: Sirona Dental Systems GmbH, Bensheim (DE)

( * ) Notice: Subject to any disclaimer, the term of this patent is extended or adjusted under 35 U.S.C. 154(b) by 83 days.

(21) Appl. No.: 12/299,886

(22) PCT Filed: Apr. 11, 2007

(86) PCT No.: PCT/EP2007/053527

§ 371 (c)(1),
(2), (4) Date: Nov. 6, 2008

(87) PCT Pub. No.: WO2007/128644

PCT Pub. Date: Nov. 15, 2007

(65) Prior Publication Data

US 2009/0175409 A1     Jul. 9, 2009

(30) Foreign Application Priority Data

May 8, 2006   (DE) .................. 10 2006 021 639

(51) Int. Cl.
*A61B 6/14*   (2006.01)
(52) U.S. Cl. ........................... 378/38; 378/208
(58) Field of Classification Search .......... 378/38, 378/208, 39, 40
See application file for complete search history.

(56) References Cited

U.S. PATENT DOCUMENTS

| 3,530,293 | A | | 9/1970 | Wehmer ................ 250/50 |
| 3,673,408 | A | | 6/1972 | Moss .................. 250/61.5 |
| 4,599,739 | A | * | 7/1986 | Nishikawa et al. ........ 378/39 |
| 4,675,888 | A | | 6/1987 | Gästrin ................. 378/38 |
| 5,224,140 | A | | 6/1993 | Virta et al. ............. 378/38 |
| 5,325,415 | A | * | 6/1994 | Coffman ................ 378/38 |
| 5,511,106 | A | * | 4/1996 | Doebert et al. .......... 378/39 |
| 5,820,552 | A | * | 10/1998 | Crosby et al. .......... 600/407 |
| 6,169,780 | B1 | * | 1/2001 | Yoshimura et al. ........ 378/38 |
| 6,926,442 | B2 | | 8/2005 | Stöckl ................ 378/197 |
| 7,433,505 | B2 | * | 10/2008 | Yoo et al. .............. 378/38 |
| 2004/0202286 | A1 | | 10/2004 | Stöckl ................ 378/197 |

FOREIGN PATENT DOCUMENTS

| DE | 34 47 862 A1 | 7/1985 |
| DE | 36 09 260 A1 | 9/1987 |
| DE | 36 27 510 A1 | 2/1988 |
| DE | 198 44 106 A1 | 4/1999 |
| DE | 101 53 979 A1 | 5/2003 |
| EP | 0 499 595 A1 | 8/1992 |
| FR | 2090727 | 1/1972 |
| FR | 2 350 088 | 12/1977 |

\* cited by examiner

*Primary Examiner*—Chih-Cheng G Kao
(74) *Attorney, Agent, or Firm*—Fitzpatrick, Cella, Harper & Scinto (57) ABSTRACT

The invention proposes a dental X-ray apparatus comprising a patient-positioning system arranged on a support and having a forehead rest. A horizontally pivotable bearing arm is arranged on the support, and the forehead rest is in turn arranged thereon.

19 Claims, 6 Drawing Sheets

DENTAL X-RAY APPARATUS COMPRISING A PATIENT-POSITIONING SYSTEM ARRANGED ON A SUPPORT AND PROVIDED WITH A FOREHEAD REST

This Application is a National Stage filing under 35 U.S.C. §371 of International Application No. PCT/EP2007/053527, filed Apr. 11, 2007, which in turn claims the benefit of priority based on German Patent Application No. 10 2006 021 639.3, filed Aug. 8, 2006. International Application No. PCT/EP2007/053527 has been published in German, but not English, as International Publication No. WO 2007/128644A2.

TECHNICAL FIELD

The invention relates to a dental X-ray apparatus comprising a patient-positioning system mounted on a carrying member and provided with a forehead rest.

PRIOR ART

DE 3627510 A1 discloses a head-positioning device for a dental X-ray diagnosis unit for creating panoramic tomographic images, in particular. The device comprises a chin rest and a forehead rest, which are horizontally adjustable and can be aligned with the patient's head. The front section of the bracket-shaped forehead rest can rest against the forehead of the patient's head and can be adjusted to fit the latter. The chin and forehead rests are mounted on a housing, which is attached pivotally to a carriage by means of girder so that the height of the chin and the forehead rests can be adjusted. The patient's line of vision is directed toward the carriage when his forehead is leaning against the forehead rest such that the rotary unit can be rotated around the patient's head.

DE 36 09 260 A1 discloses a dental X-ray diagnosis unit for creating panoramic tomographic images of a patient's jaw. In order to facilitate positioning of the patient's head for different types of radiograph, there is provided a separate positioning member for each type of radiograph. A forehead rest and a supporting element comprising a bite block are mounted on a carrying member. When the patient's head is positioned, the patient's line of vision is directed toward a carriage mounted on a column.

DE 101 53 979 A1 discloses a dental X-ray apparatus comprising a mobile carrying structure for a mobile system for the production of radiographs. For the purpose of positioning the patient, the horizontal carrying structure has handles and a bite block. While the radiograph is being produced, the patient's line of vision is directed toward the vertical column, while the horizontal carrying structure is rotated around the patient's head.

A disadvantage of the devices mentioned above is that the patient is positioned such that his line of vision is directed toward the column.

Another disadvantage is that the aforementioned positioning devices allow small clearance for movement of the head.

It is an object of the present invention to provide a dental X-ray apparatus comprising a patient-positioning system, which ensures that the patient's head is positioned correctly with no need to change position when the image is being produced and which provides simple and clearly arranged positioning means for the operator.

SUMMARY OF THE INVENTION

This object is achieved by the features of claim 1.

According to the invention, a dental X-ray apparatus is proposed which comprises a patient-positioning system mounted on a carrying member and provided with a forehead rest. On the carrying member there is disposed a horizontally pivotable carrying arm, on which, in turn, the forehead rest is disposed.

After the patient has been positioned, the carrying arm can thus be swung horizontally toward the patient, in order to position the patient's head using the forehead rest, while the patient has a clear view away from the apparatus.

Advantageously, the carrying member can be vertically adjustable and an X-ray emitter and an image detector can be mounted on the carrying member.

The vertical position of the carrying member can thus be adapted to the height of the patient, so that the X-ray emitter and the image detector can be rotated in a horizontal plane around that region of the patient which has to be imaged.

Advantageously, the carrying arm may comprise a swivel joint, which is disposed at a distance from the carrying member laterally next to a patient's position. In the imaging position, the carrying arm passes around the patient in an arcuate manner and terminates in the region of the patient's chin, while in the entry position at least a part of the carrying arm is disposed at a distance from the patient's position.

The patient can thus be positioned with his back to the carrying member, and the carrying arm passes in an arcuate manner around the patient and terminates at the patient's chin. This facilitates patient positioning for the operator, since he has an unobstructed view of the front of the patient's head to be positioned.

Advantageously, a bite block may be disposed on the carrying arm.

In this way, further positioning means are provided in addition to the forehead rest such that more precise positioning is possible.

Advantageously, the swivel joint can comprise locking means, which cooperate in such a way with a pivoted lever mounted on the swivel arm that the pivoted lever forms a frictional connection in the imaging position of the carrying arm.

The carrying arm provided with the forehead rest is thus fixed in the imaging position so that the position of the patient's head does not change during the imaging process.

Advantageously, the pivoted lever can be spring-biased and the carrying arm can comprise an unlocking device for disconnecting the frictional connection.

The carrying arm can thus be unlocked after the radiograph has been taken and be swiveled out of the imaging position so that the patient can step away from the device.

Advantageously, the unlocking device can comprise a rotary handle disposed at the end of the carrying arm and having a transmission for an unlocking member for the pivoted lever.

The carrying arm can thus be readily unlocked by activating the rotary handle.

Advantageously, the transmission can comprise a shaft and the unlocking member can be an eccentric. Additionally, at least one eccentric adapted to cooperate with guide means for a forehead rest can be provided on the shaft for the purpose of swiveling it forward.

The use of an eccentric as an unlocking member is a reliable technical solution that is easy to achieve, thus enabling maintenance and production efforts to be minimized.

Advantageously, the eccentric for cooperation with the guide means and the eccentric for unlocking the pivoted lever can be disposed on a common shaft.

Therewith the rotational forces triggering the unlocking action are transferred in a simple and reliable manner.

Advantageously, the forehead rest can be moved away from the patient's position and the pivoted lever unlocked both by rotation of the rotary handle in the same direction.

Thus, two functions are controlled by the rotary handle and the handling of the apparatus is simplified.

Advantageously, the eccentrics can be disposed in such a way on the shaft that, starting from a patient's position, the rotary handle is rotated to first move the forehead rest to a home position located at a distance from the patient and, on further rotation of the rotary handle, to trigger the unlocking action of the pivoted lever, for which purpose the eccentrics cover a substantially non-overlapping angular range.

The rotary handle is thus rotated first to move the forehead rest away from the patient's head and then to unlock the pivoted lever.

Advantageously, the forehead rest can comprise at least one bar, which can be inserted into at least one guide means, where it is guided for vertical adjustment. Furthermore, a rest element can be connected to the bar.

By displacing the bar, the forehead rest can be individually adapted to fit the size of the patient's head.

Advantageously, the forehead rest can comprise at least one bar, which is inserted into the at least one guide means, and a rest element is provided, which is guided such that it is vertically adjustable relatively to the bar.

The forehead rest can be adapted to fit the size of the patient's head by adjusting the height of the rest element relatively to the bar.

Advantageously, an additional swivel arm for a control panel can be disposed on the carrying arm.

The control panel and the patient-positioning system are thus located in the operator's field of vision so that positioning is possible without changing the line of vision.

Advantageously, the additional swivel arm can be attached to the swivel joint in such a manner that it can swivel thereabout.

Thus another independently pivotable swivel arm is provided, on which, for example, further positioning means or the control panel can be mounted.

Advantageously, handles may be disposed on the carrying arm.

The patient can thus grasp the handles so that his position remains unchanged during the X-ray imaging process. When the patient is in a standing position, the additional orientation provided by the handles is of particular advantage.

BRIEF DESCRIPTION OF THE DRAWINGS

Exemplary embodiments of the invention are depicted in the drawings, in which.

Figure 1:
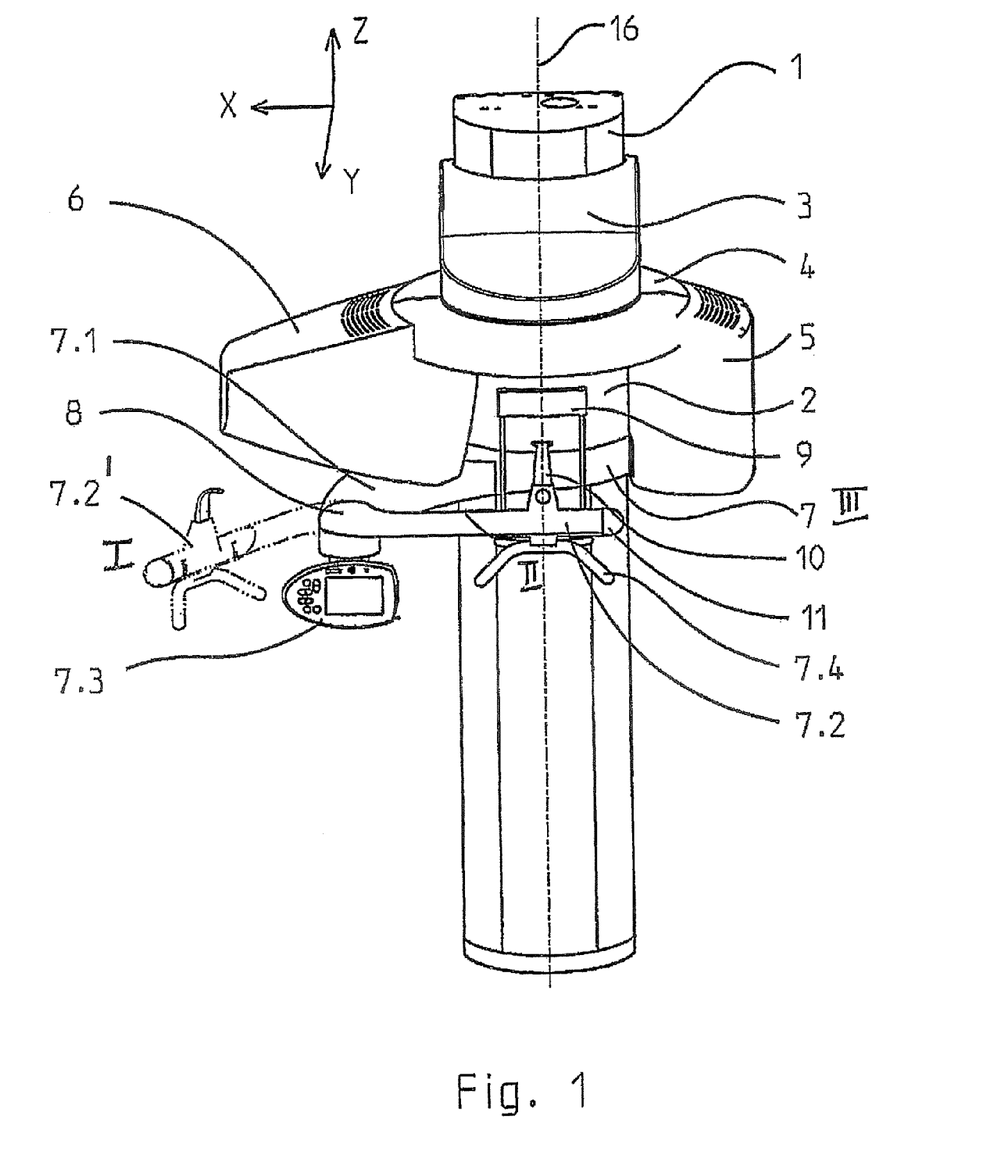
FIG. 1 shows a dental X-ray apparatus comprising a swivel arm.

FIG. 1 shows a dental X-ray apparatus. A carrying member 2 is guided on a column 1 along an axis 16 such that the carrying member 2 is vertically adjustable. A radial arm 3, on which a rotary unit 4 comprising an attached X-ray emitter 5 and an image detector 6 are disposed, is mounted on the carrying member 2. The rotary unit 4 is designed such that it can move, at least to a certain extent, along an arcuate path around a patient's head (not shown) located between the X-ray emitter 5 and the image detector 6. To the carrying member 2 there is connected a carrying arm 7, which can be vertically adjusted along with the carrying member 2. The carrying arm 7 comprises a swivel joint 8, which divides the carrying arm 7 into a fixed carrying arm section 7.1 and a swivel arm 7.2. The swivel arm 7.2 can be swiveled about the swivel joint 8 to the entry position for a patient (not shown), which position is indicated in the drawing by dot-dash lines and is designated therein by reference numeral 7.2'. In the imaging position, the swivel arm 7.2 surrounds the patient at least partly, since the swivel joint 8 is disposed to the side of the patient in a first lateral region I.

A forehead rest 9 and preferably also a bite block 10 are disposed on the swivel arm 7.2 in order to keep the patient in position during imaging. At the end of the carrying arm there is located a rotary handle 11 as part of a locking unit for the swivel joint 8, the function of which is described in detail with reference to FIG. 4.

The swivel arm 7.2 surrounds the patient and terminates with the rotary handle 11 between a central region II and a second lateral region III so that the bite block 10 on the swivel arm 7.2 can be located, in an imaging position, in the central region II.

A control panel 7.3, which enables an operator to operate the dental X-ray apparatus, is disposed on the underside of the swivel joint 8.

Furthermore, in the region of the bite block 10 on the underside of the swivel arm 7.2, there are located handles 7.4, which the patient can grasp during the X-ray imaging process so that the patient can keep his position in addition to being fixed in position by the bite block 10.

Figure 2:
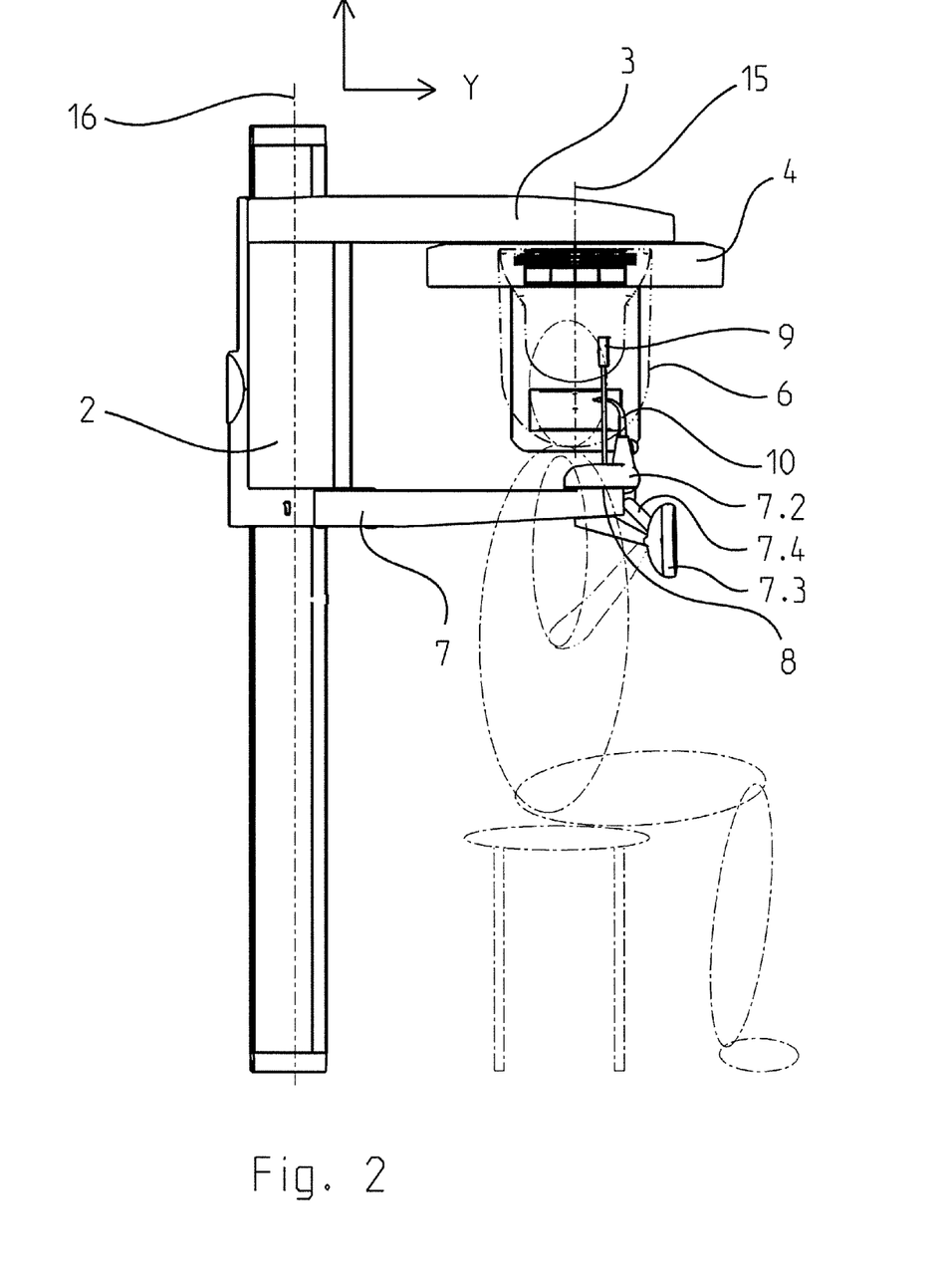
FIG. 2 is a side view of the dental X-ray apparatus shown in FIG. 1.

FIG. 2 is a side view of the dental X-ray apparatus shown in FIG. 1, again showing the column 1 with the carrying member 2 guided vertically along the axis 16. The radial arm 3 together with the rotary unit 4 is shown on the carrying member 2. In the depicted view it is looked onto the image detector 6 mounted on the rotary unit 4, which partially covers the X-ray emitter 5 (FIG. 1), the patient's head, the forehead rest 9, and the bite block 10. The rotary unit 4 rotates about the axis 15, which is parallel to the axis 16 at a distance therefrom.

The carrying arm 7 together with the swivel joint 8 and the swivel arm 7.2 can be seen on the carrying member 2. The control panel 7.3 can be seen on the underside of the swivel joint and the handles 7.4 can be seen on the swivel arm 7.2. The patient (indicated schematically) is shown in a sitting position.

Figure 3:
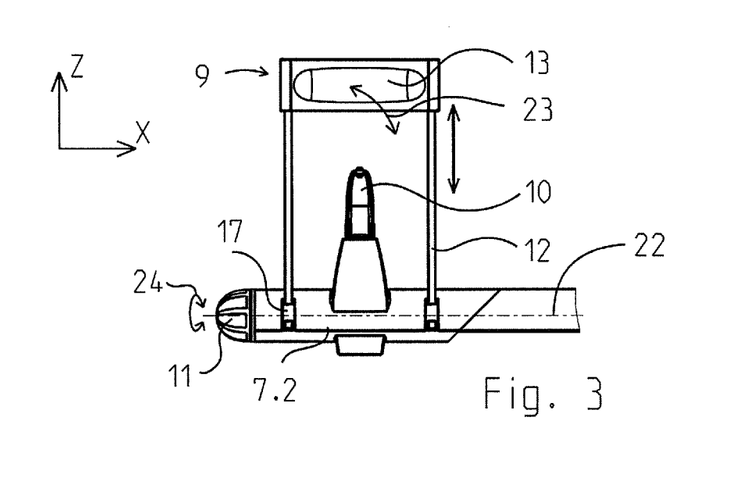
FIG. 3 shows a forehead rest and the bite block disposed at the end of the swivel arm.

FIG. 3 shows the forehead rest 9 and the bite block 10 at the end of the swivel arm 7.2 in detail. The figure shows the line of vision of the patient being in the y direction, is that is to say, from the axis 16 toward the axis 15 (FIG. 2). The forehead rest 9 comprises two spaced bars 12 disposed on the swivel arm 7.2 and on the ends of which a rest element 13 is provided. The bars 12 are guided in guide means 17 such that the bars can be vertically adjusted, and the guide means 17, together with the bars 12 and the rest element 13 can, in addition, be rotated about an axis 22 in the direction of the arrow 23 toward and away from the patient. This rotation is effected by activating the rotary handle 11 in the direction of the arrow 24.

Figure 4:
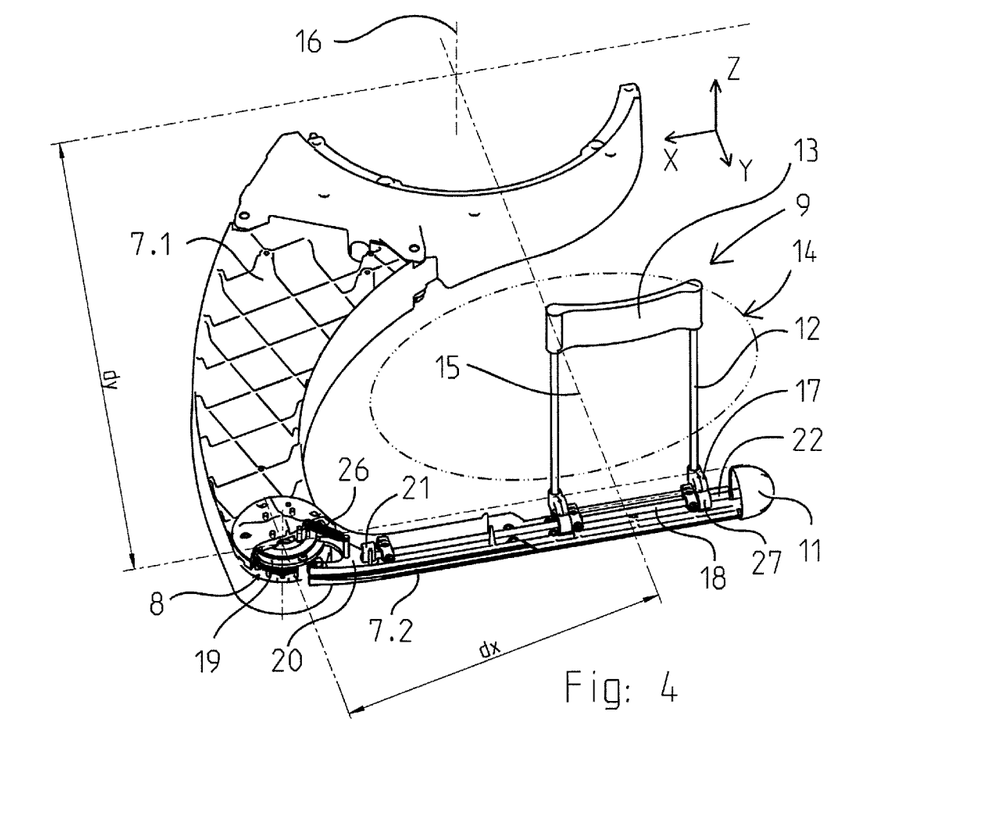
FIG. 4 illustrates the swivel joint and the rotation of the forehead rest.

FIG. 4 illustrates by way of example the swivel joint 8 on the one hand and the rotation of the forehead rest 9 on the other. The fixed carrying arm section 7.1 extends as far as the swivel joint 8 resulting in a distance dy from the carrying member. Due to the lateral arrangement of the swivel joint 8 in relation to the patient's position 14 and the axis 15, the swivel joint 8 also has a distance dx.

The swivel joint 8 comprises a toothed lock washer 19, which is firmly attached to the carrying arm section 7.1 and which cooperates with a pivoted lever 20 on the swivel arm 7.2. The swivel arm 7.2 is mounted for rotation between the toothed lock washer 19 and the carrying arm section 7.1.

The pivoted lever 20 is pressed by a spring 26 against the toothed lock washer 19, by which means a frictional connection or form fit is produced. The pivoted lever 20 is pressed by means of an eccentric 21 counter to the spring force 26 to disengage the teeth of the toothed lock washer 19, as a result of which the frictional connection or form fit is disconnected. For this purpose, the eccentric 21 is disposed on a shaft 18, which is rotated by the rotary handle 11.

The swivel arm 7.2 also carries the forehead rest 9, whose guide means 17 for the bars 12 carrying the rest 13 each cooperate with an eccentric 27. The eccentric 27 is non-rotatably connected to the shaft 18, and when the shaft 18 is rotated by means of the rotary handle 11, the guide means 17 are swiveled about the axis of rotation 22, which is parallel to the shaft 18. The axis of rotation is shown in FIG. 6.

Figure 5:
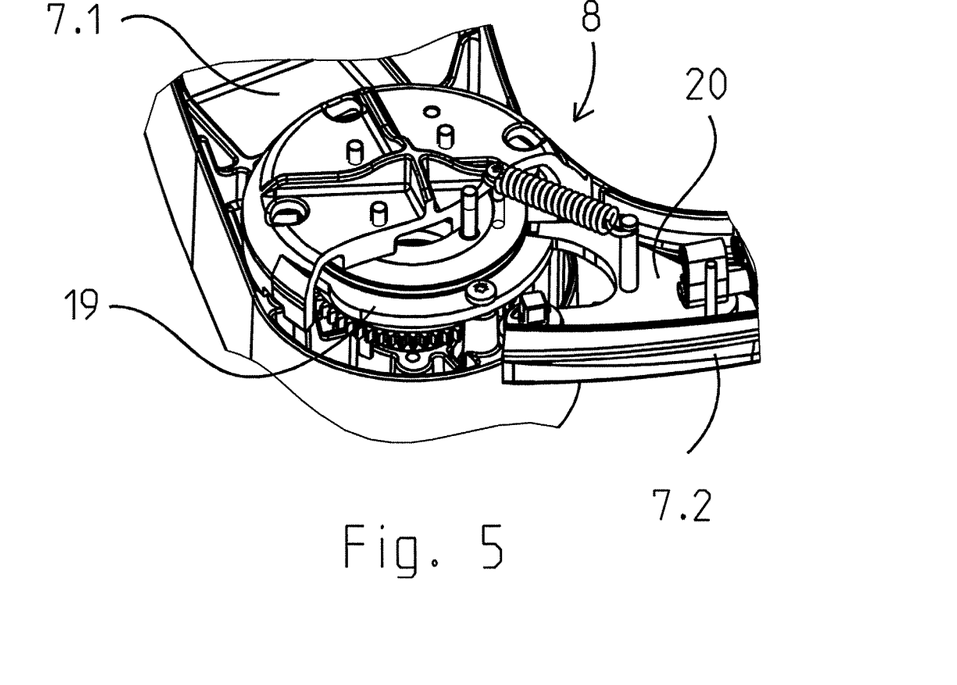
FIG. 5 illustrates the cooperation of the toothed lock washer with the pivoted lever in detail.

FIG. 5 illustrates in detail the cooperation of the toothed lock washer 19 with the pivoted lever 20. The carrying arm section 7.1 supports the firmly attached toothed lock washer 19 and the swivel arm 7.2 is disposed on bearings therebetween. Furthermore, the pivoted lever 20 is pivotally mounted on the swivel arm 7.2. In the position illustrated, the pivoted lever 20 engages the toothed lock washer 19, thereby producing a frictional connection or form fit.

Figure 6:
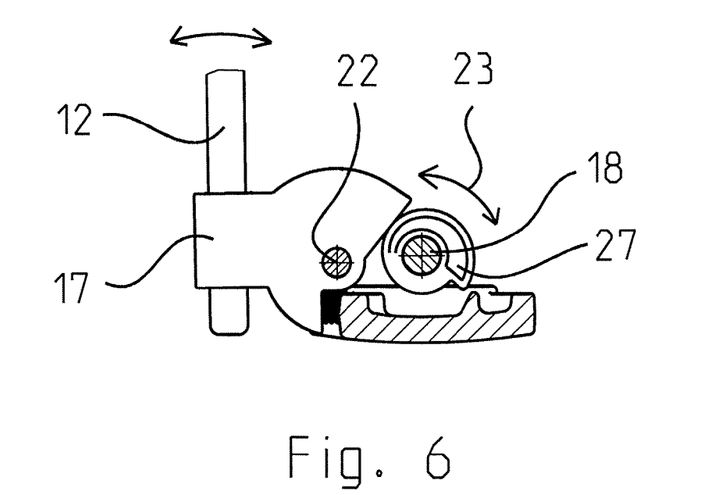
FIG. 6 shows the swiveling mechanism of the forehead rest in detail.

FIG. 6 shows the swiveling mechanism of the forehead rest in detail. The guide means 17 pivoted about a shaft 22 and one end thereof rests against the eccentric 27, which is firmly attached to the shaft 18. When the eccentric 27 is rotated by rotating the shaft 18 by means of the rotary handle (not shown), the eccentric 27 is rotated in the direction of the arrow 23 so that the bar 12 is swiveled either toward or away from the patient about the axis 22. This is effected by guiding a contact surface of the guide means 17 against the eccentric 27. The guide means 17 can be retrieved by means of a return spring (not shown), for example.

Figure 7:
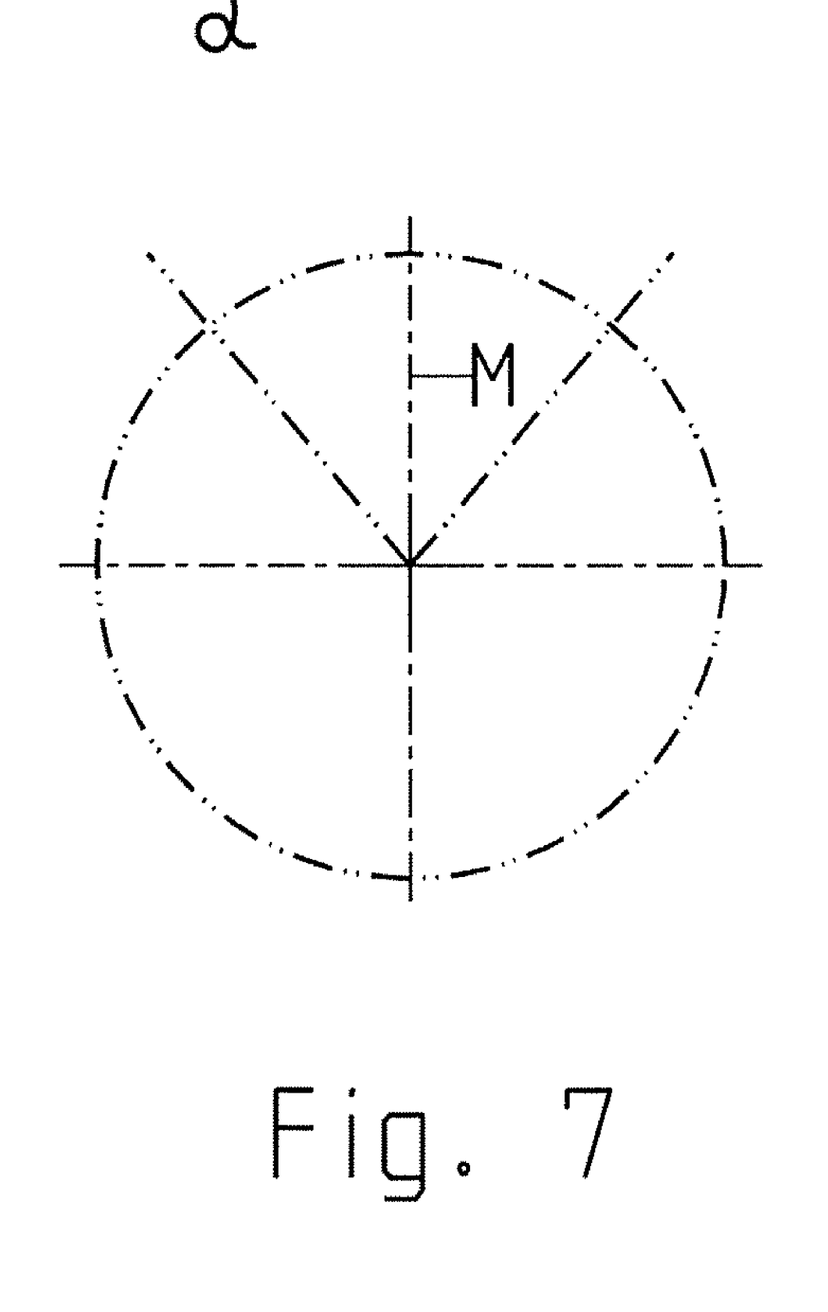
FIG. 7 illustrates diagrammatically the allocations of the angle of rotation of the rotary handle.

FIG. 7 schematically shows the division of the scope of angular rotation of the rotary handle 11 shown in FIG. 1. In a first angular range α, the forehead rest 9 shown in FIG. 3 is swiveled starting from a central position M in the entry position of the swivel arm 7.2 shown in FIG. 1, that is, when the swivel arm 7.2 is open or when the swivel arm 7.2 has just been closed by rotating the rotary handle preferably in the direction of the patient and the forehead rest 9 has been brought into contact with the patient's forehead. The angular range α is such that it is in practice fully utilized only in extreme cases. Usually, only partial swiveling within the angular range α is sufficient in order to hold the patient's forehead in the desired position. The forehead rest 9 is swiveled away from the patient to a vertical end position by rotating the rotary handle 11 in the opposite direction.

The second angular range β adjoins the angular range a without overlapping, and an angular range located therebetween may also be present. When the rotary handle is turned through the angular range A, the lock on the swivel joint 8 shown in FIG. 1 is released.

If the rotary handle is rotated further into the angular range A, the pivoted lever 20 shown in FIG. 4 is guided by way of the eccentric 21, which is shown in FIG. 4 and is connected to the shaft 18 shown in FIG. 4, from the locked position to release the swivel joint 8 so that the swivel arm 7.2 can be pivoted out of its imaging position to an entry position in order to enable the patient to enter and leave the device.

The single actuating element in the form of the rotary handle 11 can thus be used both to adjust the forehead rest 9 and to unlock the swivel arm 7.2. Furthermore, the forehead rest 9 is moved to a home position at a distance from the patient before unlocking the swivel arm 7.2.

Figure 8:
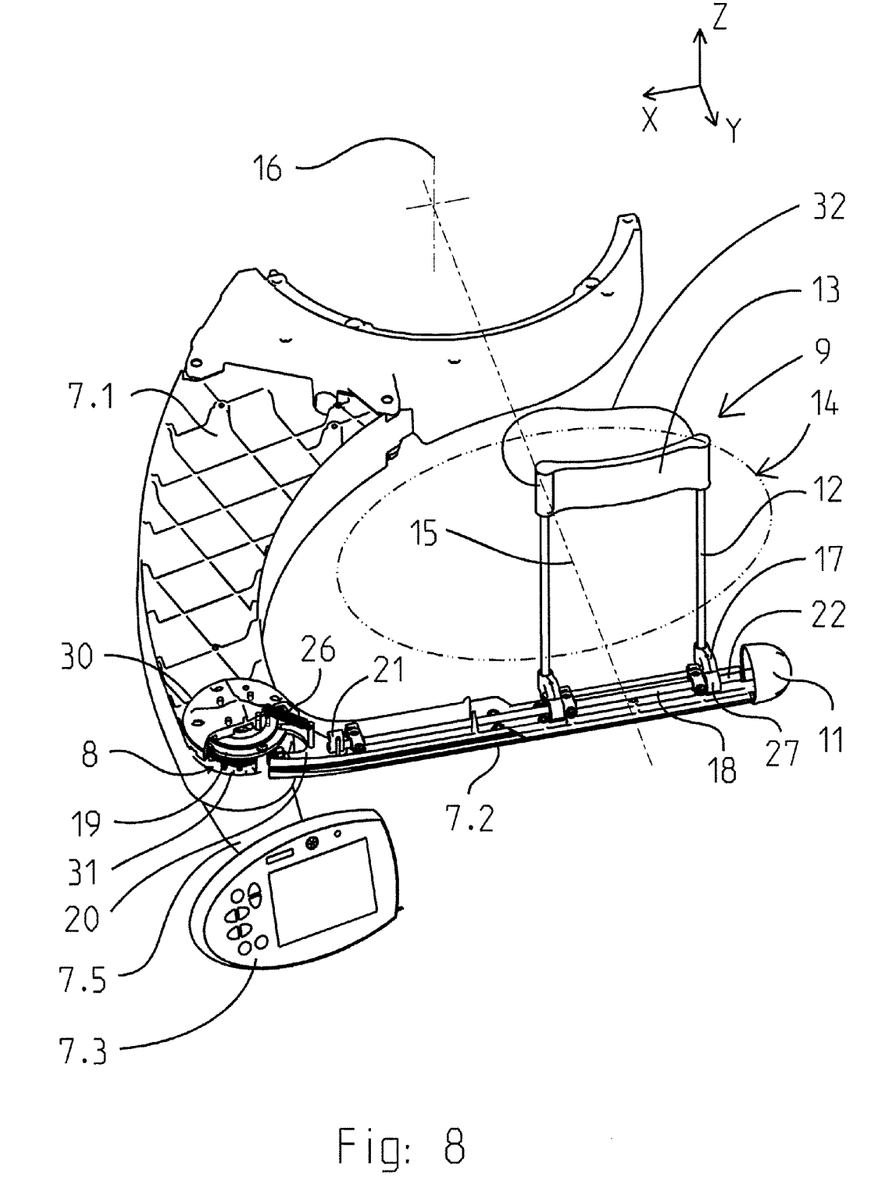
FIG. 8 shows a second swivel arm for a control panel, which is disposed on the carrying arm.

FIG. 8 shows the possibility of placing another swivel arm 7.5, for the control panel 7.3, in addition to the swivel arm 7.2, on the carrying arm section 7.1. The additional swivel arm 7.5 can then be pivotably attached to the swivel joint 8. For this purpose, the swivel joint 8 can comprise an upper bearing 30 and a lower bearing 31, to which the swivel arms are independently mounted. The swivel arm 7.2 for the forehead rest 9 can be disposed above the swivel arm 7.5 for the control panel.

It is further possible to couple the swiveling motion of the swivel arm 7.2 with that of the swivel arm 7.5 for the control panel, for example, in order to move the control panel away from the patient when opening the swivel arm 7.2. This may be effected, for example, by means of a simple entrainer provided on the swivel arm 7.2 or in the swivel joint.

In order to stabilize patients who find it difficult to keep still, a resilient belt 32 may in addition be provided, this being placed around the patient's head and hooked onto appropriate hooks on the forehead rest 9 under slight tension.

1 column
2 carrying member
3 radial arm
4 rotary unit
5 X-ray emitter
6 image detector
7 carrying arm
7.1 section of carrying arm
7.2 swivel arm
7.2' swivel arm in the entry position
7.3 control panel
7.4 handles
7.5 swivel arm
8 swivel joint
9 forehead rest
10 bite block
11 rotary handle
12 bars
13 rest
14 patient's position
15 axis of rotary unit 4
16 axis of carrying member 2
17 guide means
18 shaft
19 toothed lock washer
20 pivoted lever
21 excentric
22 axis of rotation
23 arrow
24 arrow
26 spring
27 excentric
30 upper bearing
31 lower bearing
32 resilient belt
I first lateral region
II central region
III second lateral region

The invention claimed is:

1. A dental X-ray apparatus, comprising:
   a carrying member and a forehead rest for patient-positioning,
   wherein a horizontally pivotable carrying arm is disposed on said carrying member,
   wherein said forehead rest is disposed on said horizontally pivotable carrying arm,
   wherein said horizontally pivotable carrying arm includes a swivel joint, a fixed carrying arm, and a swivel arm,
   wherein said swivel joint enables said swivel arm to pivot horizontally with respect to said fixed carrying arm, and
   wherein said swivel joint is disposed at a distance from said carrying member in a first lateral region next to a patient's position.

2. The X-ray apparatus as defined in claim 1, wherein said carrying member is vertically adjustable and an X-ray emitter and image detector are mounted on said carrying member.

3. The X-ray apparatus as defined in claim 1 or claim 2, wherein said horizontally pivotable carrying arm, in an imaging position, passes around the patient's position in an arcuate manner and extends beyond a central region of the patient's position.

4. The X-ray apparatus as defined in claim 1, wherein said horizontally pivotable carrying arm terminates at a commencement of a second lateral region of said patient's position opposite said first lateral region, and said swivel arm, in an entry position, is disposed at a distance from said patient's position.

5. The X-ray apparatus as defined in claim 1, wherein a bite block is disposed on said horizontally pivotable carrying arm.

6. The X-ray apparatus as defined in claim 1, wherein said swivel joint includes a locking mechanism.

7. The X-ray apparatus as defined in claim 6, wherein said locking mechanism includes locking means cooperating with a pivoted lever on said horizontally pivotable carrying arm such that said pivoted lever creates, in an imaging position of said horizontally pivotable carrying arm, a frictional connection or a positive fit.

8. The X-ray apparatus as defined in claim 7 wherein said horizontally pivotable carrying arm includes an unlocking device for disconnecting said frictional connection.

9. The X-ray apparatus as defined in claim 8, wherein said unlocking device has a rotary handle disposed at an end of said horizontally pivotable carrying arm.

10. The X-ray apparatus as defined in claim 9, wherein said unlocking device includes a transmission device extending to said unlocking member for said pivoted lever.

11. The X-ray apparatus as defined in claim 10, wherein said transmission device is a shaft and said unlocking member is an eccentric.

12. The X-ray apparatus as defined in claim 11, wherein at least one further eccentric is provided on said shaft, said at least one further eccentric cooperating with guide means for a forehead rest for swinging said forehead rest forward.

13. The X-ray apparatus as defined in claim 12, wherein said rotary handle is adapted, when rotated in one specific direction, both to move said forehead rest away from said patient's position and to unlock said pivoted lever.

14. The X-ray apparatus as defined in claim 13, wherein said eccentrics are disposed on said shaft such that, starting from the patient's position, rotation of said rotary handle first moves said forehead rest to a home position at a distance from said patient's position and then, on further rotation, unlocks said pivoted lever and said eccentrics cover a substantially non-overlapping angular range ($\alpha$, $\beta$).

15. The X-ray apparatus as defined in claim 12, wherein said forehead rest includes at least one bar which can be pushed into at least one guide means, wherein said at least one bar is guided for vertical adjustment, and wherein a rest is connected to said bar.

16. The X-ray apparatus as defined in claim 12, wherein said forehead rest includes at least one bar, which is inserted into said at least one guide means and wherein a rest is provided which is vertically adjustable relatively to said bar.

17. The X-ray apparatus as defined in claim 1, wherein another swivel arm is disposed on said horizontally pivotable carrying arm for a control panel.

18. The X-ray apparatus as defined in claim 17, wherein said other swivel arm is pivotably attached to said swivel joint.

19. The X-ray apparatus as defined in claim 1, wherein handles are disposed on said horizontally pivotable carrying arm.

* * * * *